United States Patent [19]
Kawai et al.

[11] Patent Number: 5,369,490
[45] Date of Patent: Nov. 29, 1994

[54] CONTOUR MEASURING APPARATUS

[75] Inventors: Masaharu Kawai, Kanagawa; Katsuya Miyoshi, Tokyo; Masami Baba, Saitama, all of Japan

[73] Assignee: Nikon Corporation, Tokyo, Japan

[21] Appl. No.: 51,247

[22] Filed: Apr. 23, 1993

[30] Foreign Application Priority Data

May 29, 1992 [JP] Japan .................. 4-138479

[51] Int. Cl.⁵ .............................................. G01B 11/24
[52] U.S. Cl. ...................... 356/376; 250/561; 433/29
[58] Field of Search .............. 356/375, 2, 376, 377, 356/380, 384, 385, 30; 250/560, 561, 563; 433/29, 24, 44, 68, 223, 214, 72

[56] References Cited

U.S. PATENT DOCUMENTS

3,867,032  2/1975  Bruck .................... 356/30

FOREIGN PATENT DOCUMENTS

| | | |
|---|---|---|
| 0107820 | 5/1984 | European Pat. Off. |
| 0299490 | 1/1989 | European Pat. Off. |
| 0411889 | 2/1991 | European Pat. Off. |
| 0207608 | 8/1989 | Japan ........................ 356/376 |
| 0162247 | 6/1990 | Japan ........................ 356/376 |

*Primary Examiner*—Richard A. Rosenberger
*Assistant Examiner*—Hoa Q. Pham
*Attorney, Agent, or Firm*—Shapiro and Shapiro

[57] ABSTRACT

A contour measuring apparatus comprises a laser measurement unit, a mount table for mounting an object, a motor for rotating the mount table around an axis, an altering jig for supporting the mount table and the motor and altering a direction of the axis with respect to the laser measurement unit, and a drive table for supporting the altering jig and driving the altering jig to alter a position of the mount table with respect to the laser measurement unit. A method for measuring contour comprises the steps of measuring a top plane contour of the object by the above contour measuring apparatus to obtain top plane contour data relating to a top plane measurement coordinate system, measuring a side plane contour of the object by the contour measuring apparatus to obtain side plane contour data relating to a side plane measurement coordinate system, and making the top plane and side plane measurement coordinate systems coincident to obtain overall contour data of the object in accordance with the top plane contour data and the side plane contour data.

24 Claims, 5 Drawing Sheets

CONTOUR MEASURING APPARATUS

BACKGROUND OF THE INVENTION

1. Field of the Invention

The present invention relates to a contour measuring apparatus.

2. Related Background Art

In the contour measurement of an object, for example, a tooth, the following apparatus are used: (a) a three-dimensional measuring apparatus by a contact type probe, (b) a measuring apparatus by a micrometer, (c) a measuring apparatus by an interference fringe of a light, (d) a measuring apparatus by image processing of camera photographing, and (e) a 5-plane measuring apparatus by a laser.

In the apparatus (a), an apparatus which measures five planes instead of one plane is available, but because it is of contact type, it is necessary to finely sample the object in order to measure it with a high precision, and hence it takes a long time for measurement (approximately 10 hours).

FIG. 1 illustrates a principle of the 5-plane measurement. In FIG. 1, numeral 1 denotes a tooth. FIGS. 2A and 2B illustrate the 3-dimensional measurement by a 3-dimensional measuring apparatus having a contact type probe. In FIG. 2A, numeral 2 denotes a contact type probe. In FIG. 2B, numeral 3 denotes grid-like measurement points. Of the grid-like measurement points 3, the points outside the tooth 1 are not measured.

In the apparatus (b), an object or the tooth 1 is mounted on a position changing table 4 and it is measured by applying a needle 5 of a micrometer to the measurement points while the table 4 is driven step by step. Accordingly, the precision of the measurement is low and the measurement time is long. FIG. 3 illustrates the measurement by a micrometer.

In the apparatus (c), the measurement precision around the contour of the object or the tooth 1 is low as shown in FIG. 4. In FIG. 4, numeral 6 denotes an interference fringe.

In the apparatus (d), the precision is low due to the manual measurement as shown in FIG. 5. As shown, a person must trace an outline 9 of an image 8 of the tooth 1 displayed on a display screen 7, by a pen 10.

In the apparatus (e), the apparatus is of large scale because of the necessity to measure five planes and the apparatus is expensive.

SUMMARY OF THE INVENTION

It is an object of the present invention to provide a compact and inexpensive contour measuring apparatus which solves the above problems encountered in the prior art and permits high precision measurement in a short time.

In order to solve the above problems, the contour measuring apparatus of the present invention comprises a mount table for an object (a hold means for holding an object), a rotating means for the mount table, an altering means for a rotation axis of the mount table, an altering means for a position of the mount table, and a laser measurement unit.

The measurement by the present contour measuring apparatus is carried out in the following manner.

The object is mounted on the mount table (hold means) and the object is non-contact measured by a laser on an upper plane and side planes thereof, while the laser measurement unit is fixed at a point in a space.

In the measurement of the object on the upper plane thereof, the rotation axis of the motor (rotation means) for rotating the mount table is vertical and the direction of movement of the drive table for altering the position of the mount table is fixed horizontally. The measurement is done by irradiating a laser to a circumference centered at the center of rotation of the motor on a plan view while the object mounted on the mount table is rotated by the motor and the drive table is kept stationary. Then the drive table is finely driven horizontally, and the measurement of the circumference is done in the same manner while the object is rotated and the drive table is kept stationary. By repeating the above process, the upper plane measurement of the object over the entire plane is done.

In the side plane measurement of the object, the rotation axis of the motor for rotating the mount table is horizontal, and the direction of movement of the drive table is horizontal as it is in the top plane measurement. The measurement is done by irradiating the laser to a predetermined one of points having the same horizontal coordinate measured from an origin point of a measurement system or a side elevational view while the object is rotated by the motor and the drive table is kept stationary. Then, the drive table is finely driven horizontally and another point having the same horizontal coordinate is measured while the object is rotated and the drive table is kept stationary. The above process is repeated to measure the object over the entire side plane.

The upper plane and side plane data thus measured are normalized by the coordinates so that they are available as 3-dimensional contour data.

In the measurement by the present apparatus, high precision contour data can be attained in a short time by the measurement of only two planes, the top plane and the side plane. Since the present apparatus is simple in construction, it can be manufactured with a low cost. Further, since it is compact, it is suitable for the measurement of a small item such as a tooth.

DETAILED DESCRIPTION OF THE PREFERRED EMBODIMENT

A preferred embodiment of the present invention explained below.

Figure 1:
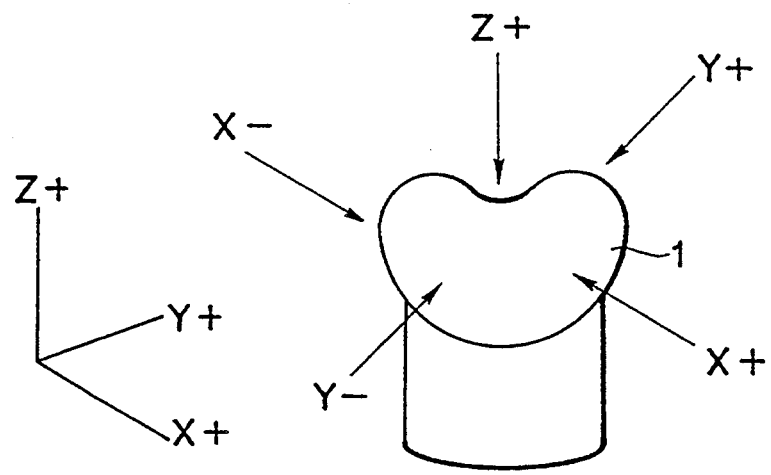
FIG. 1 illustrates a principle of prior art 5-plane measurement.
Figure 2A:
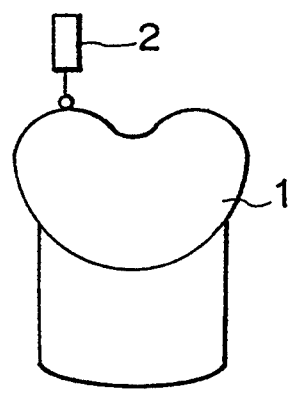
FIGS. 2A and 2B illustrate the measurement by a prior art 3-dimensional measuring system having a contact type probe.
Figure 2B:
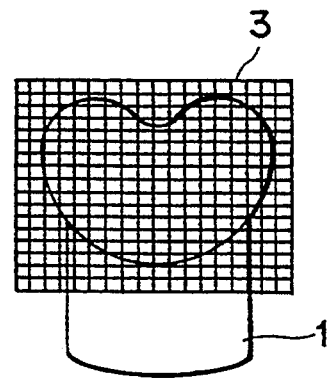
Figure 3:
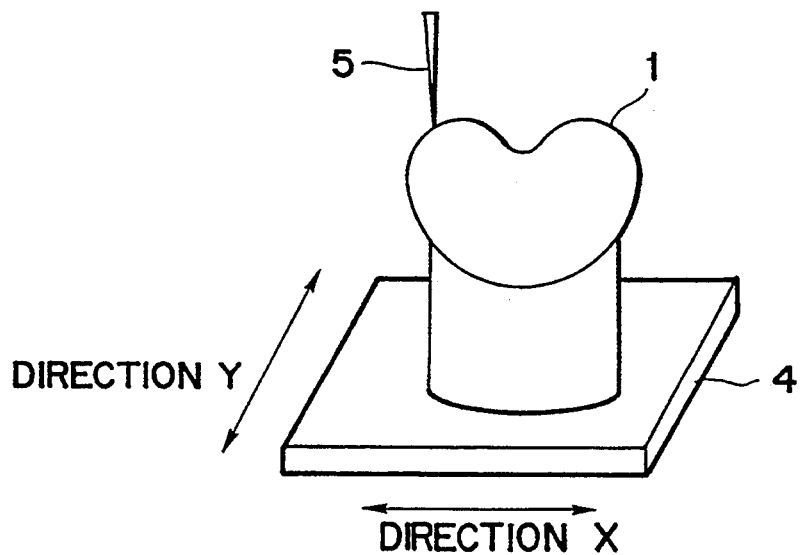
FIG. 3 illustrates the measurement by a prior art micrometer.
Figure 4:
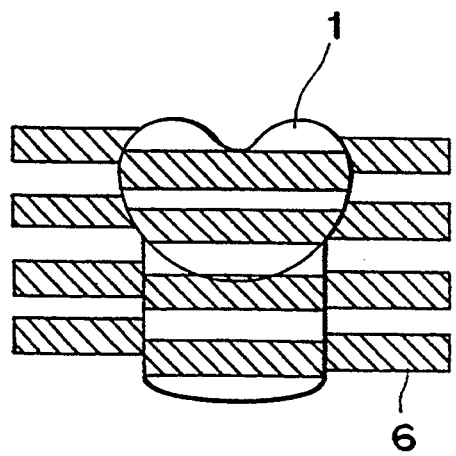
FIG. 4 illustrates the measurement by a prior art measuring apparatus by an interference fringe of a light.
Figure 5:
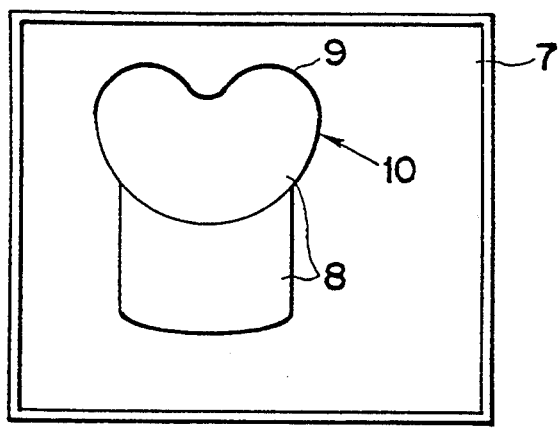
FIG. 5 illustrates the measurement by a prior art measuring apparatus by image processing of camera photographing.
Figure 6A:
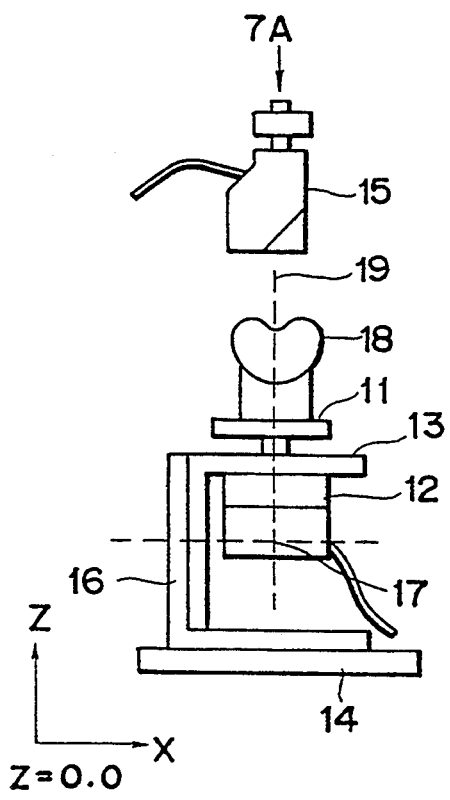
FIGS. 6A and 6B show schematic side views of a contour measuring apparatus in accordance with one embodiment of the present invention.
Figure 6B:
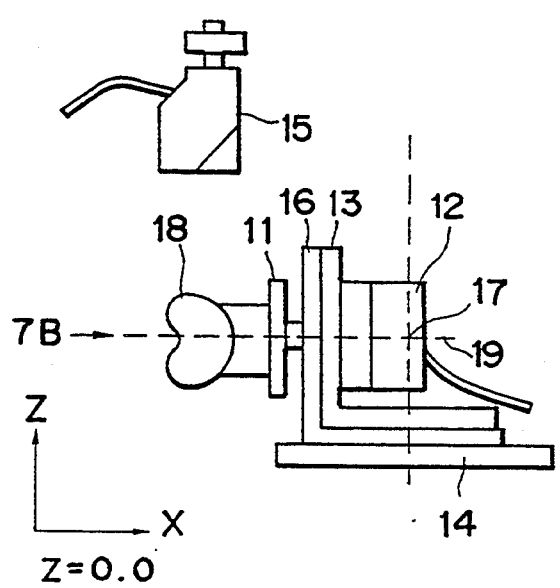

FIGS. 6A and 6B show a contour measuring apparatus of the present embodiment. It comprises a mount table (hold means) 11 to permit the rotation of an object, the alteration of a rotation axis and the alteration of a position, a motor (rotation means) 12 for rotating the mount table, a drive table (drive means) 14 for altering the position of the mount table, an altering means 13 for altering the mount table rotation axis, a fixed jig 16 and a laser measurement unit 15.

An object or a tooth 18 is mounted on the mount table 11. The rotation axis can be rotated by 90 degrees by the altering means 13 for the mount table rotation axis, which is fixed to the drive table 14 by the fixed jig 16.

The contour of the tooth 18 is measured by the present contour measuring apparatus in the following manner. An origin point of the measurement system is set at a center 17 of rotation of the rotation axis of the motor so that the measurement of the laser at that point is zero.

Figure 7A:
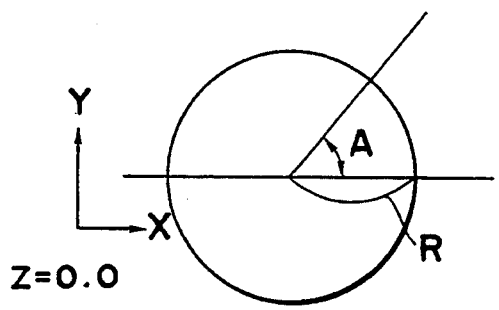
FIG. 7A illustrates a coordinate system as viewed along an arrow 7A of FIG. 6A.
Figure 7B:
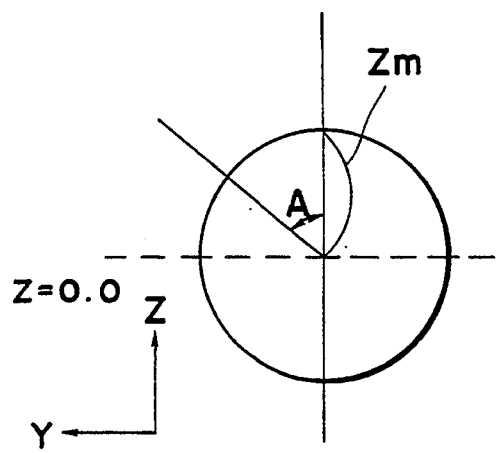
FIG. 7B illustrates a coordinate system as viewed along an arrow 7B of FIG. 6B.

In order to carry out the top plane (clench plane) measurement of the tooth 18, the tooth 18 is mounted on the mount table 11 with a face-up position. The motor 12 is rotated one revolution and the Z-coordinate (vertical) is measured by the laser. In the first rotation, the measurement is for only one point (a center of concentric circles). After one revolution, the drive table 14 is stepped along the X axis and the motor 12 is rotated. The measurement for Z-coordinate on a circle having a radius equal to the displacement R of the drive table 14 is done. As shown in FIG. 7A, X and Y coordinates are calculated as follows:

$$X = R \cdot \cos A$$

$$Y = R \cdot \sin A$$

R: displacement of drive table 14
A: rotation angle of motor 12

Figure 8A:
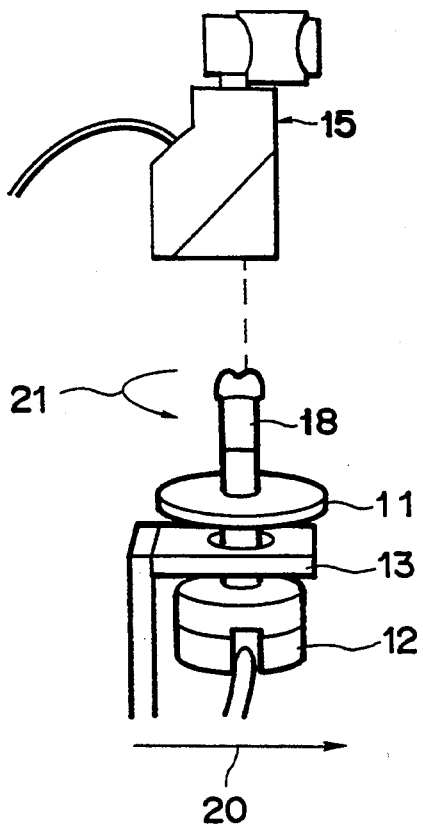
FIGS. 8A and 8B show perspective views to illustrate the measurement of a tooth by the contour measuring apparatus in the embodiment of the present invention.
Figure 9:
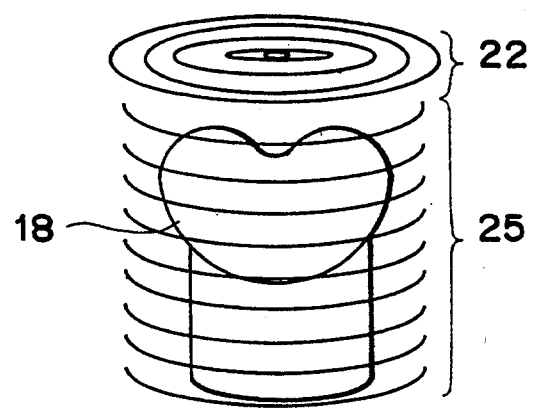
FIG. 9 illustrates the measurement scan of the tooth by the contour measuring apparatus in the embodiment of the present invention.

The drive table 14 is then moved one step at a time along the X axis and similar measurement is done over the entire plane of the tooth 18 to complete the top plane measurement (see FIGS. 8A and 9). Then, the drive table 14 is returned to the original position.

FIG. 8A illustrates a non-contact measuring method for measuring a clench plane of the tooth 18 by a laser sensor. Each time the drive table 14 is stepped along an arrow 20, the tooth 18 is rotated one revolution in a direction of an arrow 21 by the motor 12 and the clench plane of the tooth 18 is measured by the laser measurement unit 15. Thus, the measurement scan is concentric as shown by 22 in FIG. 9.

Then, in order to carry out the side plane (axial plane) measurement of the tooth 18, the rotation axis of the mount table (which is same as the rotation axis of the motor) is rotated by 90 degrees around the Y axis into the horizontal position by the altering means 13 for altering the mount table rotation axis.

Further, the apparatus is adjusted such that the laser measurement (Z axis) of the center 17 of rotation of the rotation axis of the motor, which is the origin point of the measurement system, is zero. The motor 12 is rotated one revolution and the laser is irradiated to another point having the same horizontal coordinate as measured from the origin point 17 of the measurement system on the side elevational view. The X, Y and Z coordinates are calculated as follows.

$$X = X_0 + R$$

$$Y = Zm \cdot \sin A$$

$$Z = Zm \cdot \cos A$$

where $X_0$: X coordinate of measurement point
R: Displacement of drive table 14
Zm: Laser measurement
A: Rotation angle of motor 12

Figure 8B:
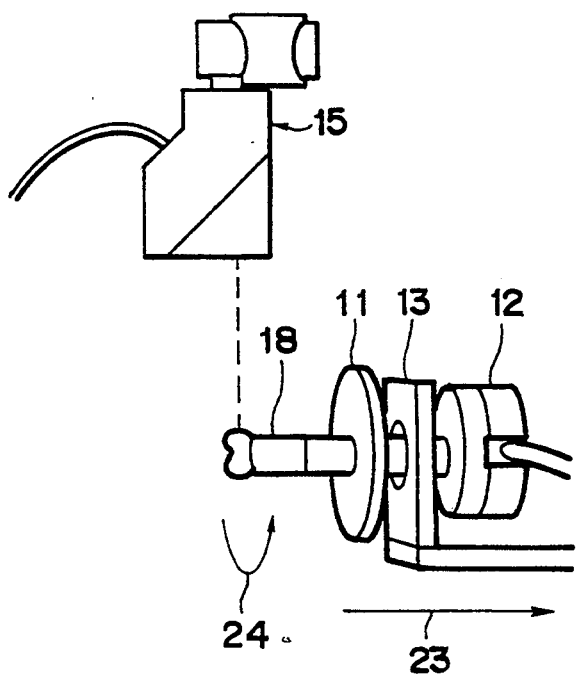

Then, the drive table 14 is stepped in the X direction and similar measurement is done over the entire side plane of the tooth 18 to complete the side plane measurement (FIGS. 8B and 9).

FIG. 8B illustrates a non-contact measuring method for measuring the side plane or the axial plane of the tooth 18 by a laser sensor. Each time the drive table 14 is stepped in the direction of an arrow 23, the axial plane of the tooth 18 is measured by the laser measurement unit 15 while the tooth 18 is rotated by the motor 12 in the direction of the arrow 24. As a result, the measurement scan is cylindrical as shown by 25 in FIG. 9.

Finally, the resulting measurement data for the side plane is rotated 90 degrees around the Y axis to make the coordinate systems of the measurement data of the top plane and the side plane coincident.

$$(Xa, Ya, Za) = (Xb, Yb, Zb) \cdot \text{rot (90 degrees)}$$

where rot (90 degrees): operator for processing 90-rotation of coordinate system around Y axis
(Xb, Yb, Zb): measurement before coordinate transform
(Xa, Ya, Za): measurement after coordinate transform As discussed above, the contour measuring apparatus of the present invention comprises the mount table (hold means) for the object, the rotation means for the mount table, the altering means for the rotation axis of the mount table, the altering means for the position of the mount table and the laser measurement unit. The measurement by the present apparatus attains the high precision contour data in a short time by the measurement of only two planes, the top plane and the side plane. Since the apparatus is simple in construction, it can be manufactured at a low cost. Further, since it is compact, it is suitable for the measurement of a small object such as a tooth.

What is claimed is:

1. A contour measuring apparatus comprising:
a laser measurement unit;
hold means for holding an object;
rotation means for rotating said hold means around a predetermined axis;
altering means for supporting said hold means and said rotation means and altering a direction of said predetermined axis with respect to said laser measurement unit; and
drive means for supporting said altering means and driving said altering means to alter the position of said hold means with respect to said laser measurement unit, wherein said altering means can take a first position in which said predetermined axis is parallel to a laser beam emitted from said laser measurement unit and a second position in which said predetermined axis is perpendicular to the laser beam emitted from said laser measurement unit.

2. A contour measuring apparatus according to claim 1, wherein said altering means includes a support member for supporting said hold means and said rotation means, and fixing means for fixing said support member to said drive means.

3. A contour measuring apparatus according to claim 1 wherein said drive means steps perpendicularly to a laser beam emitted from said laser measurement unit.

4. A contour measuring apparatus according to claim 1 wherein said rotation means includes a motor.

5. A contour measuring apparatus according to claim 1, wherein said hold means holds a tooth.

6. A method for measuring contour comprising the steps of:
providing a contour measuring apparatus including a laser measurement unit, hold means for holding an object, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit;
measuring a top plane contour of an object with said contour measuring apparatus to obtain top plane contour data relating to a top plane measurement coordinate system;
measuring a side plane contour of the object with said contour measuring apparatus to obtain side plane contour data relating to a side plane measurement coordinate system; and
making said top plane and side plane measurement coordinate systems coincident to obtain overall contour data of the object in accordance with said top plane contour data and said side plane contour data.

7. A method for measuring contour comprising the steps of:
providing a contour measuring apparatus including a laser measurement unit, hold means for holding a tooth, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit;
measuring a top plane contour of a tooth with said contour measuring apparatus to obtain top plane contour data relating to a top plane measurement coordinate system;
measuring a side plane contour of the tooth with said contour measuring apparatus to obtain side plane contour data relating to a side plane measurement coordinate system; and
making said top plane and side plane measurement coordinate systems coincident to obtain overall contour data of the tooth in accordance with said top plane contour data and said side plane contour data.

8. A method for measuring contour comprising the steps of:
providing a contour measuring apparatus including a laser measurement unit, hold means for holding an object, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit, wherein said altering means can take a first position in which said predetermined axis is parallel to a laser beam emitted from said laser measurement unit and a second position in which said predetermined axis is perpendicular to the laser beam emitted from said laser measurement unit;
measuring a top plane contour of an object with said contour measuring apparatus to obtain top plane contour data relating to a top plane measurement coordinate system;
measuring a side plane contour of the object with said contour measuring apparatus to obtain side plane contour data relating to a side plane measurement coordinate system; and
making said top plane and side plane measurement coordinate systems coincident to obtain overall contour data of the object in accordance with said top plane contour data and said side plane contour data.

9. A method for measuring contour comprising the steps of:
providing a contour measuring apparatus including a laser measurement unit, hold means for holding an object, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit, wherein said altering means includes a support member for supporting said hold means and said rotation means, and fixing means for fixing said support member to said drive means;
measuring a top plane contour of an object with said contour measuring apparatus to obtain top plane contour data relating to a top plane measurement coordinate system;
measuring a side plane contour of the object with said contour measuring apparatus to obtain side plane contour data relating to a side plane measurement coordinate system; and
making said top plane and side plane measurement coordinate systems coincident to obtain overall contour data of the object in accordance with said top plane contour data and said side plane contour data.

10. A method for measuring contour comprising the steps of:
providing a contour measuring apparatus including a laser measurement unit, hold means for holding an object, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit, wherein said drive means steps perpendicularly to a laser beam emitted from said laser measurement unit;

measuring a top plane contour of an object with said contour measuring apparatus to obtain top plane contour data relating to a top plane measurement coordinate system;

measuring a side plane contour of the object with said contour measuring apparatus to obtain side plane contour data relating to a side plane measurement coordinate system; and making said top plane and side plane measurement coordinate systems coincident to obtain overall contour data of the object in accordance with said top plane contour data and said side plane contour data.

11. A method for measuring contour comprising the steps of:

providing a contour measuring apparatus including a laser measurement unit, hold means for holding an object, rotation means for rotating said hold means around a predetermined axis, altering means for supporting said hold means and said rotation means and altering a direction of said predetermined axis with respect to said laser measurement unit, and drive means for supporting said altering means and driving said altering means to alter the position of said hold means with respect to said laser measurement unit, wherein said rotation means includes a motor;

measuring a top plane contour of an object with said contour measuring apparatus to obtain top plane contour data relating to a top plane measurement coordinate system;

measuring a side plane contour of the object with said contour measuring apparatus to obtain side plane contour data relating to a side plane measurement coordinate system; and making said top plane and side plane measurement coordinate systems coincident to obtain overall contour data of the object in accordance with said top plane contour data and said side plane contour data.

12. A method for measuring contour comprising the steps of:

a) providing a laser measurement unit in a predetermined position;

b) rotating an object around a predetermined axis extending in a first direction while measuring a first plane contour of the object with said laser measurement unit to obtain first plane contour data relating to a first plane measurement coordinate system;

c) shifting the object in a linear direction transverse to said first direction and repeating step b);

d) altering the direction of said predetermined axis to a second direction transverse to said first direction;

e) rotating the object around said predetermined axis extending in said second direction while measuring a second plane contour of the object with said laser measurement unit to obtain second plane contour data relating to a second plane measurement coordinate system;

f) shifting the object in a linear direction transverse to said first direction and repeating step e); and g) making said first plane and second plane measurement coordinate systems coincident to obtain overall contour data of the object in accordance with said first plane contour data and said second plane contour data.

13. A method for measuring contour according to claim 12, wherein, in each of said shifting steps, the object is shifted in said second direction.

14. A method for measuring contour according to claim 13, wherein said first direction and said second direction are perpendicular.

15. A method for measuring contour according to claim 14, wherein said first direction is parallel to a laser beam emitted from said laser measurement unit.

16. A method for measuring contour according to claim 12, wherein said laser measurement unit constitutes part of a contour measuring apparatus including hold means for holding the object, rotation means for rotating said hold means around said predetermined axis, altering means for supporting said hold means and said rotation means and altering the direction of said predetermined axis with respect to said laser measurement unit to correspond with said first direction and said second direction, and drive means for supporting said altering means and driving said altering means to alter the position of said holding means with respect to said laser measurement unit to effect the shifting of steps c) and f).

17. A method for measuring contour according to claim 16, wherein, in each of said shifting steps, the object is shifted in said second direction.

18. A method for measuring contour according to claim 17, wherein said first direction and said second direction are perpendicular.

19. A method for measuring contour according to claim 18, wherein said first direction is parallel to a laser beam emitted from said laser measurement unit.

20. A method for measuring contour according to claim 12, wherein the object is a tooth.

21. A contour measuring apparatus comprising:

a laser measurement unit;

hold means for holding an object;

rotation means for rotating said hold means around a predetermined axis;

altering means for supporting said hold means and said rotation means and altering a direction of said predetermined axis with respect to said laser measurement unit; and drive means for supporting said altering means and shifting said altering means in a linear direction transverse to a direction of a laser beam emitted by said laser measurement unit and thereby shifting said hold means in said linear direction transverse to the direction of said laser beam.

22. A method for measuring contour according to claim 21, wherein said altering means includes a support member for supporting said hold means and said rotation means, and fixing means for fixing said support member to said drive means.

23. A method for measuring contour according to claim 21, wherein said shifting direction is perpendicular to the direction of said laser beam.

24. A method for measuring contour according to claim 21, wherein said hold means holds a tooth.

* * * * *